United States Patent [19]
Delahaye

[11] Patent Number: 5,697,785
[45] Date of Patent: Dec. 16, 1997

[54] DENTAL PROSTHESIS AND MATERIAL FOR MAKING IT

[76] Inventor: Arnaud Delahaye, 90, boulevard Maurice-Barrés, 92200 Neuilly-sur-Seine, France

[21] Appl. No.: 428,224
[22] PCT Filed: Sep. 2, 1994
[86] PCT No.: PCT/FR94/01036
§ 371 Date: May 1, 1995
§ 102(e) Date: May 1, 1995
[87] PCT Pub. No.: WO95/06453
PCT Pub. Date: Mar. 9, 1995

[30] Foreign Application Priority Data

Sep. 3, 1993 [FR] France .................. 93 10537

[51] Int. Cl.[6] .................. A61C 13/08; A61C 5/00
[52] U.S. Cl. .................. 433/212.1; 433/228.1
[58] Field of Search .................. 433/212.1, 218, 433/219, 222.1, 226, 228.1

[56] References Cited

U.S. PATENT DOCUMENTS

| 4,267,097 | 5/1981 | Michl et al. | 260/42.15 |
| 4,350,532 | 9/1982 | Randklev | 106/30 |
| 4,364,731 | 12/1982 | Norling et al. | 433/218 |
| 4,820,744 | 4/1989 | Kubota et al. | 522/13 |
| 5,043,361 | 8/1991 | Kubota et al. | 522/10 |
| 5,228,907 | 7/1993 | Eppinger et al. | 106/35 |
| 5,539,017 | 7/1996 | Rheinberger et al. | 523/116 |

*Primary Examiner*—Nicholas D. Lucchesi
*Attorney, Agent, or Firm*—Larson & Taylor

[57] ABSTRACT

The invention relates to a dental prosthesis and to a material for making it. It applies to a dental prosthesis of the type comprising a metal support, and at least one reconstruction mass fixed to the metal support, at least the major portion of the reconstruction mass being made of a composite material containing a polymer binder in which an inorganic filler is dispersed. According to the invention, the reconstruction mass has a bending strength of not less than 100 MPa, and it possesses a Vickers hardness which is not less than 450N/mm$^2$. The invention is applicable to dental prostheses.

9 Claims, 1 Drawing Sheet

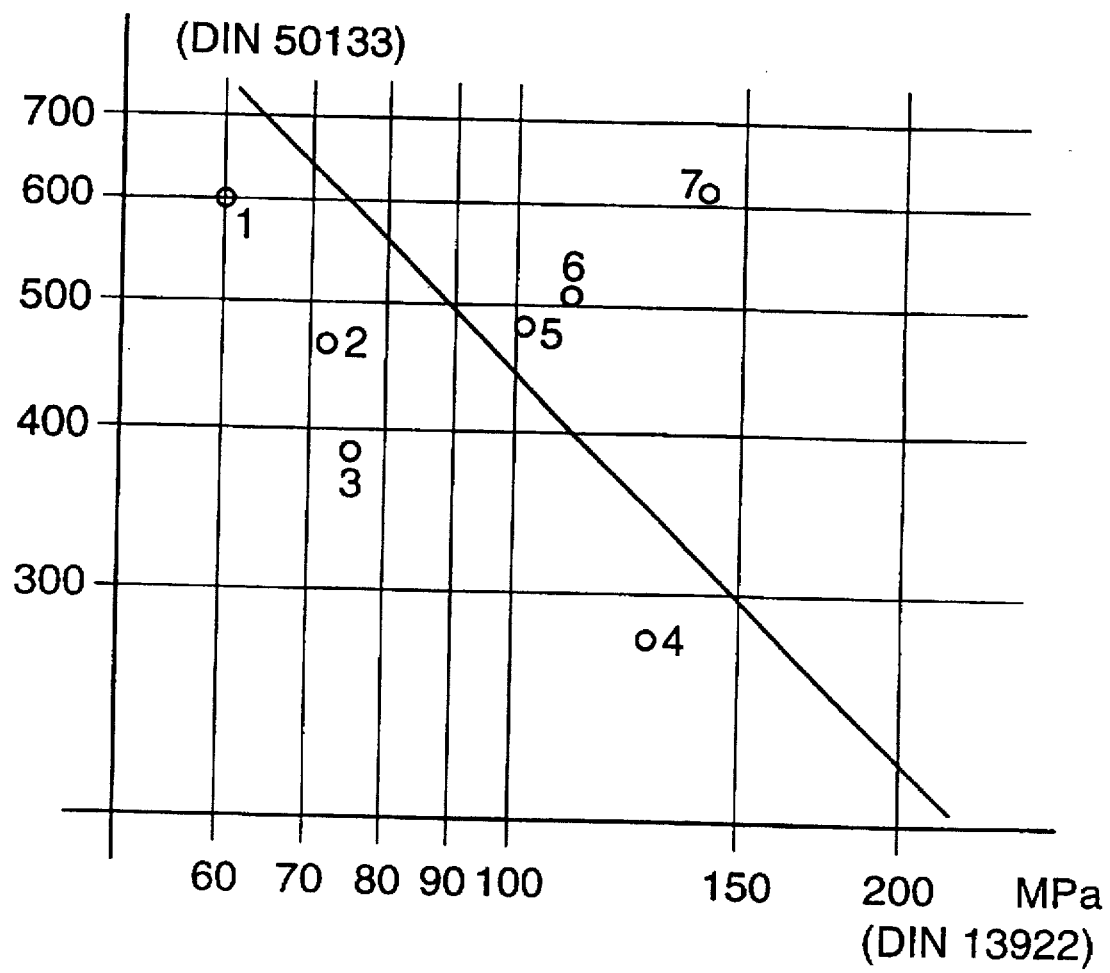

1

DENTAL PROSTHESIS AND MATERIAL FOR MAKING IT

BACKGROUND OF THE INVENTION

1. Field of the Invention

The present invention relates to dental prostheses, and to composite materials for making them.

Before describing the invention, it is appropriate to explain the terminology used in the present text including terms used by the person skilled in the art.

Dental care essentially comprises the field of repairing and reconstructing teeth proper, and the field of prosthetic reconstructions. Repairs cover fillings (classes I to V), inlays and onlays, and facings.

Prosthetic reconstructions cover both fixed prostheses and removable prostheses. Such reconstructions have a metal portion and usually involve several teeth, but they may also concern one tooth only. They are fixed to one or more teeth. They may also be fixed to one or more implants. Such reconstructions are also referred to as "prostheses" in the present text.

2. Statement of the Prior Art

The invention relates to prosthetic reconstructions of the fixed type. Such fixed type reconstructions generally comprise a metal support made by casting a metal or an alloy, and a reconstruction mass fixed to the support and which may be made out of various different materials. The materials most commonly used for such fixed reconstructions are ceramics. Plastics are also used, and sometimes also composites.

All such fixed reconstructions suffer from drawbacks.

Ceramics reconstructions are very rigid and have insufficient bending strength. They must be fixed on teeth that have been thoroughly consolidated. Nevertheless, when people are fitted with such a reconstruction that is large in size, they generally have and continue to have problems with the periodontium (alveolysis) with or without thickening of the periodontal ligament, and frequently with more or less pronounced mobility of the teeth. Installing such a ceramic reconstruction on teeth consolidated in this way leads to a high failure rate.

Reconstructions made of plastics are most advantageous from the point of view of rebuilding teeth since once such a prosthesis has been worn for a certain amount of time, it is observed that tooth mobility is reduced, as is alveolysis and the periodontal space. It is sometimes even possible to make a ceramic prosthesis on teeth that have been consolidated in this way by carrying a plastics prosthesis for a certain length of time. However, such a plastics prosthesis wears very quickly, and therefore cannot constitute a long-term solution, but merely a solution that is provisional or temporary.

Between these two extremes of behavior, attempts have already been made to use other materials having wear rates that are smaller than those of plastics while still being less rigid and more flexible than ceramics.

Thus, French patent No. 2 427 357 is concerned with the poor properties of hardness, bending strength, and resistance of the synthetic materials that were in use at that time (1978). That patent suggests using a thermosetting composition designed for dental purposes and suitable for use in "certain prostheses". The composition includes a "reinforcing filler" constituted by glass fibers or glass microspheres. The quantity of the reinforcing filler used lies in the range 1% to 50%, and preferably in the range 15% to 40%. The mechanical properties obtained are only a little better than those of the synthetic materials on their own.

Subsequently, composite materials have been used for these purposes, i.e. materials comprising a polymer binder containing an inorganic filler, and serving to make reconstructions. One of the substances giving the best results at present is sold under the trademark "Dentacolor" (Heraeus-Kulzer). However, these substances are too rigid, and it is common for them to fracture, in the same manner as can happen with reconstructions made of ceramics. In addition, their wear resistance is insufficient for very long duration reconstructions. They have therefore been used very little for reconstructions.

European patent application No. 102 199 relates to dental repair compositions stated to have excellent mechanical properties. Nevertheless, that document describes a composition which is intended solely for dental repairs, i.e. for fillings and analogous work, and it is not a composition that is intended in any way for prostheses. There is nothing in that document to suggest making a prosthesis.

SUMMARY OF THE INVENTION

Given the properties of fixed reconstructions known from work prior to the invention, an investigation has been undertaken to determine what properties a material ought to possess in order to enable prostheses or reconstructions to be made that suffer neither from the drawbacks of ceramic reconstructions nor from the drawbacks of reconstructions made of plastics, while nevertheless retaining the advantages thereof. More precisely, the advantages of ceramic prostheses are their low rate of wear and their strength over a very long period of time, while the advantages of plastics prostheses are their flexibility and the consolidation of tooth-supporting tissue (periodontium) to which they give rise. In addition, in order to be suitable for use in making a prosthesis, a material must possess all the usual properties of materials used in dentistry, in particular from the points of view of health, chemistry, and appearance.

After using known ceramics, composite, and plastics materials, it has thus been determined, according to the invention, that to enable a prosthesis to be made having the advantages both of ceramic prostheses and of plastics prostheses, the properties which a material must possess are essentially properties of bending strength and of hardness. Thus, according to the invention, it has been determined that a reconstruction mass made from a composite material must possess a bending strength of not less than 100 MPa and a Vickers hardness of not less than 450N/mm$^2$.

It has thus been understood that certain composite materials recently put on the market solely for repairs (fillings, inlays, onlays, facings) could also be used, under certain conditions, for making fixed prosthetic reconstructions or prostheses, since they enable original physical properties to be obtained necessary for making prostheses. In addition, since such materials are already in use for repairs, they possess all the health, chemical, and appearance properties required for replacements.

More precisely, the invention relates to a dental prosthesis which comprises a metal support and a reconstruction mass fixed to the metal support, the reconstruction mass being made, for the most part, out of a composite material containing a polymer binder having an inorganic filler dispersed therein. According to the invention, the reconstruction mass has a bending strength of not less than 100 MPa, and it possesses a Vickers hardness of not less than 450N/mm$^2$.

The metal support used for making the prosthesis may be of any type. It may be made of a nickel chromium alloy.

However, it is preferable for it to be made of gold, e.g. of "Protor", having a yellow color that gives a pleasing appearance to reconstruction masses placed on the metal.

The mass is preferably fixed to the metal support by interposing a keying layer. It is advantageous for the keying layer to be constituted by silica applied by pyrolysis and treated with silane.

The replacement mass is usually formed by applying successive layers which are polymerized one after another. The first layer applied on the keying layer is preferably an opaque layer, and the following layers are colored layers and/or transparent layers.

The polymer binder of the reconstruction mass is advantageously formed by polymerizing monomers that contain methacrylate esters. Polymerization is advantageously performed by photopolymerization.

The inorganic filler contained in the polymer binder is preferably in the form of a finely ground borosilicate glass. Advantageously, the mean particle size of the glass lies in the range 0.02 µm to 2 µm. Furthermore, it is advantageous for the mineral filler also to contain a small quantity of silica, advantageously treated with a silane.

To obtain the necessary hardness, it is preferable for the quantity of mineral filler to be not less than 55% by volume of the replacement mass. Advantageously, it is not less than 60% by volume. Given the nature of the fillers used, it is advantageous for the quantity of the inorganic filler to be not less than 70% by weight of the reconstruction mass, and preferably to be not less than 75% by weight.

In a variant, the reconstruction mass is subjected to tempering by prolonged irradiation, after photopolymerization of the polymer binder.

It is advantageous for the bending strength of the reconstruction mass to be about 110 MPa prior to tempering. Nevertheless, it is advantageously subjected to tempering that imparts a bending strength thereto of about 140 MPa.

It is also advantageous for the hardness of the reconstruction mass to be about 500N/mm$^2$ in the non-tempered state. However, in the tempered state, this hardness may reach or exceed 600N/mm$^2$.

The invention also relates to a photopolymerizable composite material for manufacturing a prosthesis of the type described in the preceding paragraphs.

BRIEF DESCRIPTION OF THE DRAWING

Certain essential characteristics of the invention are now described in greater detail with reference to the accompanying drawing whose sole FIGURE is a graph showing how various materials are classified as a function of their properties of hardness and of bending strength.

DETAILED DESCRIPTION OF THE INVENTION

It is known that ceramic prostheses have a Vickers hardness that can be greater than that of the reconstruction mass used in the invention. However, the bending strength of such dental ceramics is much less than that of the reconstruction mass used in the invention. In contrast, the plastics material used for prostheses has bending strength that is much greater than that of the reconstruction mass used in the invention, but its hardness is very low. It might be thought that it would suffice to select a material having properties that lie between those of a conventional ceramic and those of the plastics material used in dentistry in order to obtain properties suitable for prostheses.

The above-mentioned composite material known as "Dentacolor" has been sold for this purpose of forming reconstruction masses of prostheses. It possesses properties lying between those of conventional ceramics and those of the plastics material used in dentistry. Nevertheless, that material suffers from the drawbacks of ceramics (too rigid) without the advantages of plastics material (consolidation of the tooth support tissue—periodontium). That "Dentacolor" composite material has bending strength that is much less than that of a composite material suitable for implementing the invention, and its hardness is also much less than that of such a material.

Implementations of various ceramic and composite materials for making dental prostheses are now considered in the following examples. In the examples, only Examples 5 to 7 correspond to the invention, with the other examples being given by way of comparison.

EXAMPLE 1

Conventional ceramics prostheses were prepared from the conventional dental ceramics "Duceram" and "Biodent" that are in common use, that are based on feldspar and on silica, and that were baked at a temperature of about 930° C.

EXAMPLE 2

Using the procedures recommended by the manufacturer, prostheses were prepared including a reconstruction mass of "Thermoresin LCII" composite material containing 70% by weight of a filler essentially based on pyrogenic silica. Its polymer binder is formed by polymerizing urethane dimethacrylate and dimethacrylate monomer. This substance is commercially available from GC International Corp. It exists in an opaque variety and in transparent varieties of various colors.

EXAMPLE 3

Using the procedures recommended by the manufacturer, prostheses were prepared including a reconstruction mass of "Dentacolor" composite material containing 51% by weight of a filler essentially constituted by pyrogenic silica, having an average grain size of about 0.04 µm. Its polymer binder is formed by polymerizing esters of polyfunctional methacrylic acid. This substance is commercially available from Heraeus-Kulzer. It exists in an opaque variety and in transparent varieties of various colors.

EXAMPLE 4

Using the procedures recommended by the manufacturer, prostheses were prepared including a reconstruction mass of "Coltène Brilliant" composite material. This substance is commercially available from Coltène Whaledent. It exists in an opaque variety and in transparent varieties of various colors.

EXAMPLE 5

Using the procedures recommended by the manufacturer, prostheses were prepared including a reconstruction mass of "Cesead" composite material containing 82% by weight of a filler of very fine inorganic particles and of organic compounds. Its polymer binder is photopolymerizable while cold. This substance is manufactured by Kuraray Co. Ltd. and is commercially available. It exists in an opaque variety and in transparent varieties of various colors.

EXAMPLE 6

Using the procedures recommended by the manufacturer, prostheses were prepared including a reconstruction mass of "Charisma" composite material. It contains 77% by weight of an inorganic filler containing ten parts of a barium and aluminum borosilicate glass for one part of silane treated silica. The particle size of the borosilicate glass lies in the range 0.02 μm to 2 μm. This substance is commercially available from Heraeus-Kulzer. It exists in an opaque variety and in transparent varieties of various colors.

EXAMPLE 7

Prostheses analogous to those of Example 6 were prepared and they were subjected to tempering by implementing procedures recommended by the manufacturer.

EXAMPLE 8

Using procedures that are commonplace in the making of prostheses, prostheses were prepared including a reconstruction mass of a plastics material essentially constituted by methacrylate polymer as commonly used for making prostheses out of plastics material.

Determination of Mechanical Properties

The mechanical properties of each of the reconstruction masses of the prostheses were then determined on test pieces, each prepared simultaneously with the corresponding reconstruction mass, and under the same conditions. These mechanical properties determined were bending strength, which was determined in application of the DIN 13922 standard, and Vickers hardness, which was determined in application of the DIN 50133 standard. A parameter was also calculated that is equal to the product of the bending strength multiplied by the Vickers hardness.

The results obtained are given in the following table.

| Mechanical properties of the examples | | | | | |
|---|---|---|---|---|---|
| | (1) | (2) | (3) | | (4) |
| Material | MPa | N/mm$^2$ | % wt | % vol | k(MPa)$^2$ |
| Ceramic Example 1 | 50–70 | 500–700 | — | — | ≈ 36 |
| Composite Example 2 | 71.5 | 464 | 70 | 55 | 33.2 |
| Composite Example 3 | 75 | 385 | 51 | 35 | 28.9 |
| Composite Example 4 | 127 | 278 | ? | ? | 35.3 |
| Composite Example 5 | 101 | 480 | 82 | 64 | 48.5 |
| Composite Example 6 | 110 | 510 | 77 | 60 | 56.1 |
| Tempered composite Example 7 | 140 | 620 | 77 | 60 | 86.8 |
| Composite Example 8 | >1000 | <30 | — | — | <30 |

(1) Bending strength (DIN 13922).
(2) Vickers hardness (DIN 50133).
(3) Mineral filler content by weight and by volume.
(4) Product of the values in columns (1) and (2).

The sole FIGURE is a log-log graph showing the results of Examples 1 to 7. The sloping line represents a value of 45 k(MPa)$^2$ for the product in column (4).

The values of the various properties given in the table show that if the various materials are classified in increasing order of bending strength, then the composite materials of Examples 5 and 6 have particularly high hardness, even in the non-tempered state. On the contrast, if the materials are classified in order of hardness, then the composite materials of Examples 5 and 6 can be seen to have exceptionally high bending strength, even in the non-tempered state.

Determination of Clinical Results

Clinical tests have been performed to validate the invention on the prostheses made in the above examples.

For ceramic prostheses of Example 1, problems were observed with the periodontium (alveolysis), with or without thickening of the periodontal ligament. Sometimes, more or less severe mobility of the teeth is often observed.

For the prostheses made of the composite materials of Examples 2 and 3, problems of prosthesis fracture were observed.

In addition, with prostheses made of the composite materials of Example 3 and above all of Example 4, significant wear was quickly observed.

With the prostheses made of the composite materials of Examples 5 to 7, consolidation was observed in the majority of cases, i.e. there was a reduction in the space between the tooth and the socket, i.e. the physiology of the periodontal ligament returned to normal, thus eliminating alveolysis and reducing the periodontal space, as when using prostheses made of plastics material. The wear of the reconstruction masses was practically negligible. Such properties have never previously been observed with conventional ceramic prostheses, nor with prostheses made of previously known composite materials.

Conclusions on the Mechanical and Clinical Tests

The results of the mechanical and clinical tests show that high hardness alone is not useful (problems posed by ceramic prostheses), while high bending strength alone is not suitable either (problems posed by prostheses made of plastics material), and that a comprise between hardness and bending strength is not sufficient either (problems posed by the prostheses of Examples 2, 3, and 4). As shown in column (4) of the table, the prostheses of the invention which give the advantageous results have a product of bending strength multiplied by hardness which is well above that of all the materials that have been used in the past for making the reconstruction masses of dental prostheses. The example of the invention having the lowest product of these properties gives a value that is greater by at least about half as much again than the values of all of the materials previously used for prostheses (ceramics, composite materials such as "Dentacolor", and plastics materials). The sole FIGURE shows clearly that materials of the invention (above the sloping line) differ from materials previously Used for the reconstruction masses of dental prostheses (beneath the sloping line).

Consequently, according to the invention, it is the combination of properties of bending strength (not less than 100 MPa) and of hardness (not less than 450N/mm$^2$) of the composite material that is the essential characteristic.

Clinical tests performed with dental repairs by the manufacturers of the composite materials of Examples 5 to 7 have shown that these materials possess excellent properties of resistance to wear and abrasion, and that they give rise to non-traumatic occlusion. These materials thus possess the best properties expected of a composite material used for repairing teeth: very high resistance to wear, even after long periods of time (two years), the lowest wear of composite materials present on the market, excellent surface characteristics and in particular excellent polishing properties, highly convenient in use, excellent appearance, with respect both to coloration and to depth of tint, etc. All of these properties continue to apply in reconstructions. They are at least equivalent to those obtained using the ceramics that are conventional for reconstructions.

Prostheses of the invention thus provide an original and particularly advantageous combination of properties since they possess the advantages of ceramic prostheses (long duration, good appearance) with those of prostheses made of plastics materials (reconstruction of the periodontal ligament, elimination of alveolysis, and closure of the periodontal space).

By way of illustration, there follows a detailed description of the making of a prosthesis of the invention using Example 6 to constitute a complete bridge.

Firstly, all the metal elements of the bridge are mounted on wax in conventional manner (cast wax). Thereafter, the metal frame is transformed into metal by the lost wax method. The frame is cleaned in a jet of steam, and is then sandblasted, still in conventional manner. The surface is then prepared for forming a keying layer based on silica, e.g. by the "Silicoater MD" method sold by Heraeus-Kulzer. After the keying layer has been formed, the method comprises forming a first layer and then generally a second layer constituted by an opacifier for hiding the metal. The opacifier of these layers may be a "Dentacolor" opaque opacifier substance, and the thickness of this layer is generally a few tenths of a millimeter. Thereafter, the "Charisma" composite material is applied in successive layers to form the reconstruction mass. To this end, the dental mechanic uses various tints (in color and transparency) of "Charisma" which are applied successively in layers of a thickness that is always less than 2 mm. Each layer is polymerized by light irradiation. The last layer serves to form the enamel. In an advantageous embodiment, the prosthesis is subjected to tempering by prolonged irradiation. After polymerization, the prosthesis is subjected to conventional finishing, essentially by polishing.

The prosthesis of the invention is thus made by a method that is essentially conventional and already known to dental mechanics. However, the properties obtained are considerably better than those of prostheses made of conventional composite materials, and in general, of any of the materials conventionally used for dental prostheses. Similarly, the prosthesis may be put into place by conventional methods, e.g. by sticking to teeth or by screwing onto dental reconstruction onlays or by sticking or screwing to implants. The prosthesis then gives comfort to the patient of a kind that cannot be obtained with any known material.

The invention thus relates to the use for reconstruction purposes of a new category of composite materials presently in use for dental repairs, thereby enabling reconstruction masses to be formed that have a bending strength of not less than 100 MPa and a Vickers hardness of not less than 450N/mm². In this new use, the composite materials provide properties which constitute an original combination that cannot be obtained with any known material for dental reconstruction. This original combination of properties is not suggested in any way by the normal use of said composite materials for the purpose of conventional repairs. It should be observed that these advantageous properties are further improved because, once cast, the support metal is subjected to no further high temperature treatment which could diminish its properties, as happens with ceramic prostheses that are baked at temperatures of about 930° C. In particular, the metal retains its advantageous properties of elasticity.

Although the invention has been described with reference to using certain particular composite materials, it applies to using other materials providing they possess the combination of properties of the invention concerning bending strength and hardness. Although the invention is not limited by any theoretical explanation that may be given for the results obtained, it would appear, as indicated in column (3) of the table that it is important for the composite material to contain a very large quantity of inorganic filler.

The invention has naturally been described and shown only by way of preferred example and any technical equivalent can be applied to its component elements without thereby going beyond the ambit of the invention.

I claim:

1. A dental prosthesis comprising a metal support, and at least one reconstruction mass fixed to the metal support, at least the major portion of the reconstruction mass being formed of a composite material containing a polymer binder having an inorganic filler dispersed therein, the prosthesis being characterized in that the reconstruction mass has a bending strength of not less than 100 MPa, and possesses a Vickers hardness of not less than 450N/mm².

2. A prosthesis according to claim 1, characterized in that said prosthesis includes a keying layer for fixing the mass to the metal support.

3. A prosthesis according to claim 1, characterized in that the polymer binder of the reconstruction mass is advantageously constituted by polymerizing monomers containing methacrylate esters.

4. A prosthesis according to claim 3, characterized in that the polymer binder of the reconstruction mass is formed by photopolymerization of monomers containing methacrylate esters, and is then subjected to tempering, after photopolymerization of the polymer binder.

5. A prosthesis according to claim 4, characterized in that the bending strength of the reconstruction mass is not less than about 110 MPa, prior to tempering, and is not less than about 140 MPa after it has been tempered.

6. A prosthesis according to claim 4, characterized in that the hardness of the reconstruction mass is not less about 500N/mm² prior to tempering, and not less than about 600N/mm² after it has been tempered.

7. A prosthesis according to claim 1, characterized in that the inorganic filler contained in the polymer binder essentially comprises a finely ground borosilicate glass.

8. A prosthesis according to claim 7, characterized in that the average particle size of the borosilicate glass lies in the range 0.02 µm to 2 µm.

9. A prosthesis according to claim 1, characterized in that the quantity of inorganic filler is not less than 55% by volume of the reconstruction mass.

* * * * *